United States Patent [19]

Boiarski

[11] Patent Number: 4,854,321

[45] Date of Patent: Aug. 8, 1989

[54] INTEGRATED OPTIC SYSTEM FOR MONITORING BLOOD GASES

[75] Inventor: Anthony A. Boiarski, Columbus, Ohio

[73] Assignee: Medex, Inc., Hilliard, Ohio

[21] Appl. No.: 282,961

[22] Filed: Dec. 2, 1988

Related U.S. Application Data

[63] Continuation of Ser. No. 875,587, Jun. 18, 1986, abandoned.

[51] Int. Cl.$^4$ .............................................. A61B 5/00
[52] U.S. Cl. ...................................... 128/634; 128/666; 128/667
[58] Field of Search ............... 128/632, 634, 665, 666, 128/667

[56] References Cited

U.S. PATENT DOCUMENTS

| Re. 31,879 | 5/1985 | Lubbers et al. | 128/633 |
|---|---|---|---|
| 3,612,866 | 10/1971 | Stevens | 128/633 |
| 3,754,876 | 8/1973 | Guenther . | |
| 4,003,707 | 10/1974 | Lubbers . | |
| 4,075,493 | 2/1978 | Wickersheim | 374/159 |
| 4,200,110 | 4/1980 | Peterson et al. | 128/634 |
| 4,201,222 | 5/1980 | Haase | 128/634 |
| 4,272,484 | 6/1981 | Lubbers | 128/633 |
| 4,272,485 | 6/1981 | Lubbers | 128/633 |
| 4,306,877 | 12/1981 | Lubbers | 128/633 |
| 4,476,870 | 1/1977 | Peterson . | |
| 4,560,248 | 12/1985 | Cramp et al. | 128/633 |
| 4,585,007 | 4/1986 | Uchigaki et al. | 128/632 |
| 4,606,351 | 8/1986 | Lubbers | 128/665 |
| 4,706,677 | 11/1987 | Goorsky et al. | 128/634 |
| 4,710,623 | 12/1987 | Lipson et al. | 128/634 |

FOREIGN PATENT DOCUMENTS 0073558 3/1983 European Pat. Off. ............ 128/634

Primary Examiner—Lee S. Cohen
Assistant Examiner—John C. Hanley
Attorney, Agent, or Firm—Wood, Herron & Evans

[57] ABSTRACT

Blood gases and the like are monitored by a single probe having multiple dye wells and dyes immobilized in the wells, the dyes being exposed to the blood gases. Optical fibers and waveguides connected to the dye wells permit light to be directed from a light source to be dyes and the light due to absorption or the spontaneous emission of the dye returned to a light detector. The intensity, phase shift or other mechanism of the returned radiation is a measure of the partial pressure of a respective blood gas.

11 Claims, 3 Drawing Sheets

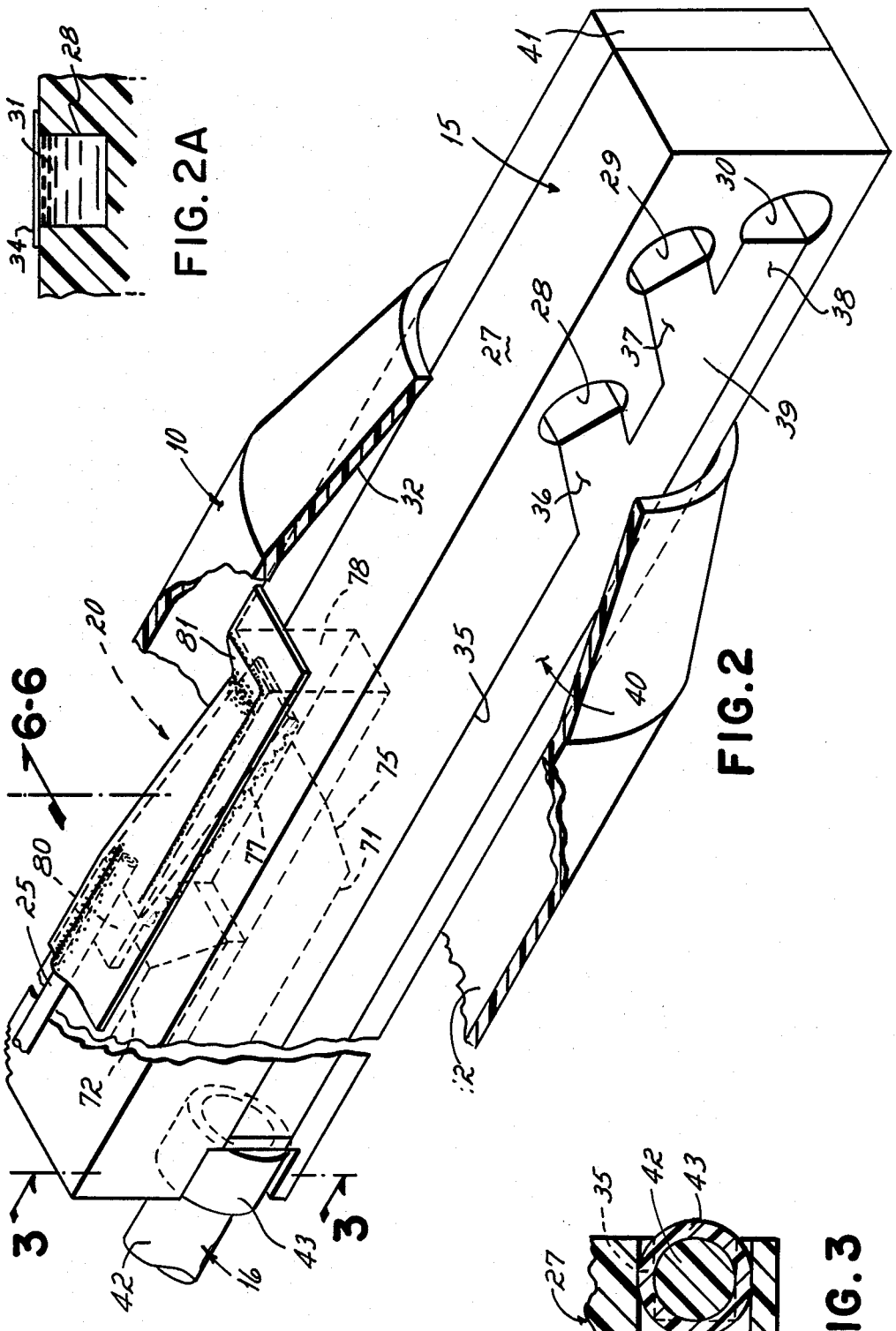

INTEGRATED OPTIC SYSTEM FOR MONITORING BLOOD GASES

This application is a continuation, of application Ser. No. 875/587, filed 6-18-86, now abandoned.

This invention relate to a probe for monitoring constituents in a bodily fluid such as blood, and more particuarly, the invention relates to a probe as part of an apparatus for continuously monitoring the constituents in the blood including, pH, $pCO_2$ and $pO_2$, blood electrolytes and blood pressure.

Over the years, considerable research and development work has been carried on in the field of monitoring gases but not necessarily restricted to blood gases. Within the last twenty years, or so, attention has been given to the development of monitoring systems having the following components: a dye to react with the constituents being monitored, a structure for holding the dye, a membrane separating the monitored analyte from the dye, and a system for directing light onto the dye and monitoring the returned radiation, the intensity of the return radiation being a measure of the constituent pasing through the membrane and contacting the dye.

Two primary systems have been proposed. In the first, a system for measuring $0_2$, for example, a fluorescent dye is excited by the incoming light source to cause it to fluoresce. The wavelength of fluorescence is different from the wavelength of the incoming light source. Oxygen will tend to qunech the intensity of fluorescence. The degree of quenching becomes a measure of the pressure of oxygen in the fluid being monitored.

Another known system employs an absorption based dye. The dye is irradiated by light of known intensity. The absorption capability of the dye is affected by the constituent whose presence is being monitored. The intensity of the incoming light is compared to the intensity of the light scattered back from the dye to determine the quantity of the constituent in the blood.

At the present time, there has been no production of a single probe which is small enough (less than a millimeter in dimension) to be inserted into a blood vessel for the continuous monitoring of the triad of pH, $C0_2$ and $0_2$. The problem appears to be that there has been no practical design for and method of manufacturing such a tiny device which satisfies all the criteria for a commercially successful device such as low cost for disposability, absence of toxicity, capability of being sterilized and the like.

It has been an objective of the present invention to provide a tiny probe having a maximum transverse dimension of about 0.625 mm and thus being capable of being passed through a 20 gauge catheter cannula whose minimum internal diameter is 0.711 mm. The probe is connected by optical fibers to monitoring apparatus and is capable of providing real time information concerning one or more constituents of blood.

It has been another objective of the invention to provide a probe for the measurement of blood pressure and mounted on the same probe as that which measures partial pressures or constituents of blood.

It has been another objective of the invention to provide a probe which is capable of holding a dye, the dye being accessible through a permeable substance, and the probe having an optical system capable of interrogating the dye.

It has been another objective of the invention to provide a method of manufacturing an integrated optic probe of the type described herein.

These objectives are attained by providing a plastic base, forming one or more dye wells in the plastic base, forming, in the plastic base, waveguides that provide light paths to the dye walls and mounting optical fibers onto the base in optical communication with the waveguides so as to bring incoming light to the dye wells and to return the radiation from the dye wells to monitoring apparatus.

The base is formed by a photofabrication process which includes the steps of forming a block of light-hardenable material, masking the portion of that material to be removed and subjecting the remainder to light to harden it. Thereafter, the masked portion is washed away, leaving one or more dye walls, as desired, and channels in the block connected to the dye walls, the channels to be subsequently formed as waveguides. A deposit of optical cement in the channel followed by the optical hardening of it creates the waveguides to the respective dye wells.

In a preferred form of the invention, a single optical fiber is cemented in the block and is connected by a main waveguide and branch waveguides to the dye wells. The dyes selected are fluorescing type dyes and are immobilized in substances that are selectively permeable to the gases under observation. A source, capable of producing multiple differing wavelengths is directed through a multiplexer to the single optical fiber to excite the dyes. The wavelengths emanating from the fluorescing dye are returned and their intensities measured to provide a measurement of the constituents being observed.

For the measurement of blood pressure, the invention provides a block having a cavity therein. The cavity is covered by a cantilevered diffraction grating and a flexible seal which flexes in response to changes in blood pressure and thereby causes the diffraction grating to pivot. Optical fibers and waveguides direct light of two wavelengths onto the diffraction grating and direct the reflected light back to measuring apparatus. A ratio of the intenstiy of the reflected beams provides a measure of the deflection of the gratings and hence blood pressure. Intensity is not the only method of determining analyte concentration. Lifetime decay (phase shift) plus others can be used.

Another feature of the invention resides in the mounting of the blood pressure monitoring probe on the blood gas monitoring probe. The mounting is such that, when passed through a cannula, the dye wells on the blood gas probe will be positioned beyond the cannula and the blodd pressure probe will remain within the cannula. A heparin solution, which is slowly introduced into the blood stream through the the blood to the probe without the cannula.

The several features and objectives of the invention will become more readily apparent from the following detail description taken in conjunction with the accompanying drawings in which:

FIG. 2 is a perspective view of the probe and cannula combination.

FIG. 2A is a fragmentary cross-sectional view illustrating a dye well.

FIG. 3 is a cross sectional view taken along lines 3—3 of FIG. 2.

GENERAL ORGANIZATION AND OPERATION

Figure 1:
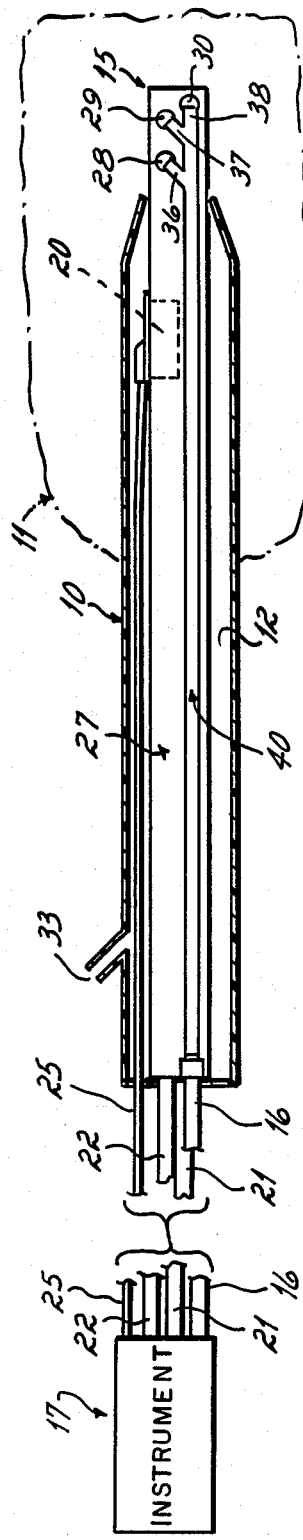
FIG. 1 is a diagrammatic elevational view illustrating the invention.

As shown in FIG. 1, a cannula 10 is inserted into the blood vessel of a patient indicated at 11. The cannula has an internal bore 12. Passing through the bore and partially projecting slightly beyond the cannula is a probe 15 which is connected by at least one optical fiber 16 to an instrument 17 whose functions will be described.

Mounted on the probe 15 is a blood pressure probe 20, and two optical fibers 21 and 22 connected to the instrument 17. Further, a tube 25 is connected to the blood pressure probe to introduce a reference pressure into the probe, as will be described below.

As best shown in FIG. 2, the blood gas probe consists of a base on block 27 in which three dye wells 28, 29 and 30 are formed. The block 27 is tiny, having a maximum dimension across the diagonal, in cross section, of about 0.625 mm. Its thickness is about 0.4 mm. thick, specifically 0.38 mm. and its width is about 0.5 mm. These dimensions permit the probe to pass through the cannula bore 12 which is about 0.90 mm. in diameter. The tip of the bore where it is tapered inwardly, as shown at 32, has a maximum diameter of about 0.711 mm. It is necessary to provide spacing between the inside diameter of the cannula tip and the outside dimensions of the probe to permit the flow of a heparin solution from an injection site 33 (FIG. 1) to the bloodstream in the artery to prevent clotting of the blood. Additionally, it may be necessary from time to time to take blood samples through the injection site 33.

Each dye well forms a sensor for a specific blood gas. Let it be assumed that dye well 28 is for sensing oxygen $O_2$, dye well 29 is for $CO_2$ and dye well 30 is for pH. Each dye well contains a dye 31 which is excited to fluorescence by an incoming beam of a preselected wavelength. The intensity of the fluorescence is measured. That fluorescence is to be selectively quenched by the particular blood gas associated with the dye.

The dye well can be covered by a membrane 34 selectively permeable for the blood gas to be measured or, alternatively and preferably, the dye can be immobilized in a porous matrix which is selectively permeable to the gas being measured. For example, the $O_2$ and $CO_2$ can be disposed in a matrix of silicone rubber. The dye for the $O_2$ is insensitive to $CO_2$. The dye for the $CO_2$ is insensitive to $O_2$. The silicone rubber is hydrophobic and will block permeation of water and the larger gas molecules.

The dye well 30 contains a fluorescing dye embedded in a porous matrix of acrylamide gel which is hydrophilic and thus permits the passage of water containing the H ion. The dye contained within the matrix is sensitive only to the hydrogen ion.

An optical channel 35 having branches 36, 37 and 38 is connected to each dye well. The channel is filled with an optical cement 39 which is hardened and which, in combination with the block which forms the channel, creates a waveguide 40 leading to each dye well. The optical fiber 16 is connected in the channel 35 in abutment with the waveguide to form a substantially loss-free optical path from the apparatus 17 to the waveguide and back.

It is contemplated that each dye well could have incoming and outgoing waveguides and a pair of optical fibers each being optically connected to a respective waveguide.

To facilitate the understanding of the operation of the blood gas monitor, a fairly basic system will be first described.

A light source within the apparatus 17 will be directed through the optical fiber and waveguide 35 to each dye well to excite the dye contained within the dye well to fluorescence. Each dye will fluoresce at its own frequency or wavelength. The intensity of the unquenched fluorescence is known. When each dye is subjected to the respective blood gas to which it is sensitive, its intensity of fluorescence will be quenched. The degree of quenching will be the measure of the partial pressure of the blood gas under observation. The foregoing system is an over simplification of the operation of the monitoring apparatus. A more specific description of the probe and its operation to measure blood gases will be sent forth hereinafter.

THE PROBE

The configuration of the probe is dictated to some extent by the size of the cannula through which it is passed. The cannula shown in FIG. 2 is about 50 mm. long and has an inside diameter of about 0.90 mm. The tip 32 is tapered and has a minimum inside diameter of 0.711 mm.

The overall dimenions of the probe are therefore preferred to be 0.38 mm. thick and 0.5 mm. wide. The length of the probe is slightly greater than 50 mm. so that the probe fills the flexible 50 mm. portion of the cannula with the three dye wells projecting beyond the tip of the cannula as shown in FIG. 2. Thus, the dye wells will be exposed to the comparatively rapid flow of blood (approximately 100 cc. per minute) as contrasted to the very slow flowing heparin solution of a few drops per minute passing through the cannula. The blood pressure probe 20, however, is preferably disposed within the cannula bore as shown. Since the pressure of the heparin solution within the cannula will be the same as the blood pressure, the blood pressure probe on the outside of the cannula does not have to be subjected directly to the blood.

Except for the substrate 41 which is an aluminum substrate, the block 27 is substantially entirely formed of a photopolymer film resist, that is, a monomer which is polymerized by ultraviolet light such as Riston manufactured by duPont. It will be flexible enough to bend with any flexure of the cannula in the artery.

Each block is formed with a channel configuration, as shown at 35–38. Each channel and branch is converted to a waveguide by filling with a photo-resist or optical cement such as Norland Optical Adhesive manufactured by Norland Products, Inc. of New Brunswick, N.J. The channel is of square cross section having a cross-sectional dimension of 0.112 mm. by 0.112 mm. A single optical fiber 16 having a core diameter of 0.112 mm. is positioned in the channel 35 and is in abutment with the waveguide formed by the polymerized Norland material. The positioning of the optical fiber should be such that its core 42 lies exactly within the confines of the square waveguide material as shown in FIG. 3 with the cladding 43 projecting beyond the waveguide.

With this configuration, all of the excitation light will pass from the core into the waveguide without loss. The return light, emitted from the fluorescing dye, will substantially entirely all return to the core except for a small loss from the light at the corners of the waveguides which do not lie in abutment with the fiber core.

Figure 4:
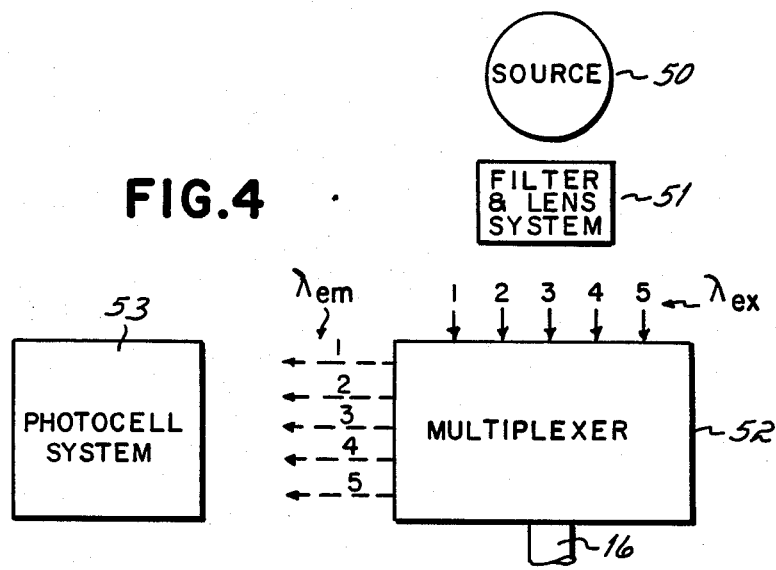
FIG. 4 is a diagrammatic view of a portion of the monitoring apparatus.

The optoelectronic system for interrogating the probe is diagrammatically illustrated in FIG. 4. As shown there, a source 50 directs light through a filter and lens system 51 to create five excitation wavelengths $\lambda ex$ 1-5. A multiplexer 52 transmits those excitation waves to the optical fiber 16 which in turn directs the wave to the dye wells. Excitation waves 1 and 2 interact with the dye in dye well 30 which monitors pH. Waves 3 and 4 interact with the dye and dye well 29 which measures $CO_2$. Wave 5 interacts with the dye well 28 which measures the oxygen $O_2$.

Each excitation wave creates a corresponding fluorescent wave which is transmitted through the waveguide 35 and the optical fiber back to the multiplexer as emitted wavelengths $\lambda em$ 1-5. These wavelengths are received by a photocell system 53 which measures their intensities.

The measurment systems for pH, $O_2$ and $CO_2$ are similar. A single source is filtered to provide excitation wavelengths. A multiplexer will sequence those wavelengths to excite the dye at different intervals of time. The fluorescene will be at a third wavelength. The intensity of the fluorescence created by the first wavelength will be different from the intensity of the fluorescence when excited by the second wavelength. The intensity of the fluorescing wavelength produced by each excitation wavelength will change with changes in concentration of $CO_2$ or pH. However, the intensity produced by one excitation wavelength will change at a rate different from the intensity produced by the other excitation wavelength. The ratio of those two intensities, assuming no variation in the intensity of the source, will be a measure of the pH and will remain constant regardless of losses occurring in the system. It is contemplated that the ratios of emitted intensities will be measured to determine pH and $CO_2$, $CO_2$ being essentially a pH measurement as is well known in the art.

The measurement of oxygen partial pressure cannot be done in that fashion. Instead, the oxygen-sensitive dye is excited by a single wavelength and the rate of decay of the emitted wave is measured. As a preliminary, it will have been determined, for the specific dye and excitation wavelength, what the rate of decay will be for different oxygen pressures. For example, if the pressure of oxygen is high, the rate of decay will be faster than if the pressure of oxygen is low. Thus, the instrument can be programmed to measure the length of time for the intensity of the emitted fluorescence to drop a preselected number of units of intensity. The time for decay, for one level of oxygen pressure, from one specified point to a lower specified point will always be the same regardless of losses in the system. Thus, when the decay times are known for the various levels of oxygen pressure, determining the decay time for an unknown blood will produce the desired information.

All of this apparatus is housed in a microprocessor-based instrument 17 that provides the necessary calculations and presents real time readouts of pH, $pO_2$, $pCO_2$ and blood pressure, as will ber described hereinafter.

THE PROCESS OF MANUFACTURE OF THE GAS PRESSURE PROBE

On of the advantages of the present invention is the low cost for producing probes. The low cost is obtained through the integrated optic design of the probe which admits of mass production techniques as disclosed hereinafter.

Figure 5:
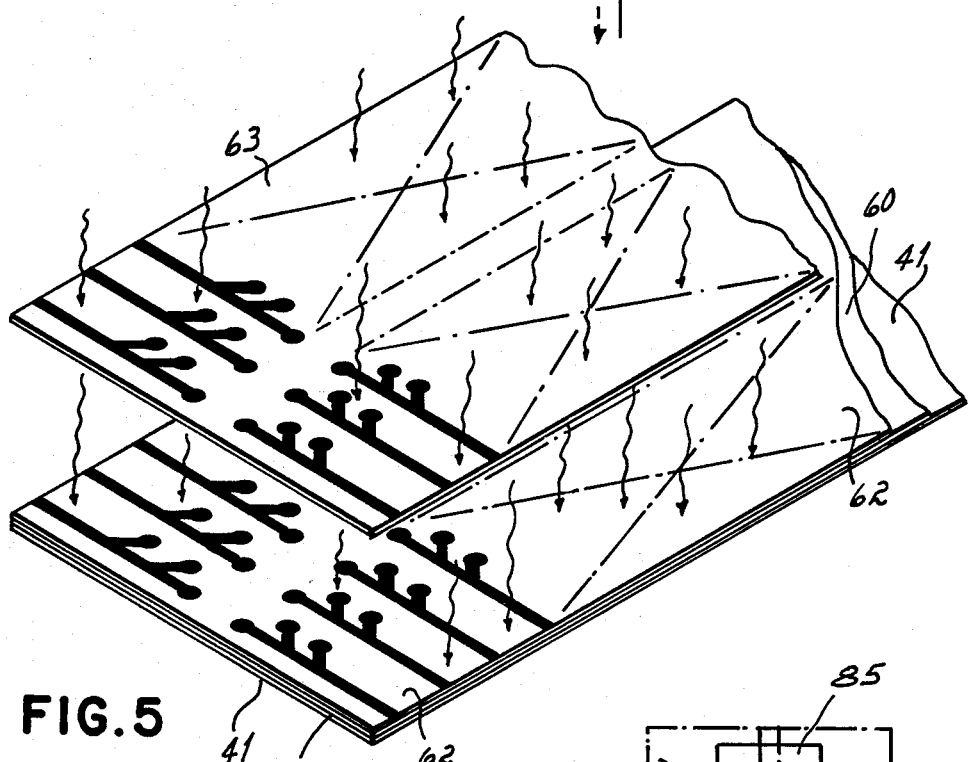
FIG. 5 is a diagrammatic view of the elements illustrating the process of manufacturing probes.

As shown in FIGS. 5, in the simultaneous manufacture of multiple probes a Riston layer 60 is mounted on an aluminum substrate 41. The Riston layer is subjected to ultraviolet light to harden it. These layers are in plan 100 mm by 200 mm and thus capable of making 800 probes having dimensions of $50 \times 0.5$ mm.

A second Riston layer 62 is applied to the Riston layer 60. It is 0.112 mm. thick which is the desired depth of each dye well and associated waveguide.

A mask 63 is applied to the Riston layer 62, the mask defining the dye wells 28, 29 and 30 and channels 35–38 to be formed for each probe. Since each probe is approximately one-half mm. wide, approximately 400 elements can be masked on one-half the strip and 400 elements masked on the other half of the strip. The thus masked strip is subjected to ultraviolet light to polymerize all unmasked portions of the strip. After exposure and hardening, the unhardened monomer is washed out with a solution with 1,1,1-trichlorethane leaving the dye wells and channels.

A photo-resist optical cement (Norland) is inserted in the dye wells and associated channels just formed.

A second mask is placed over the strip to mask each of the three dye wells and the length of channel 35 leading to the channel branches 36–38. With the strip thus masked, it is subjected to ultraviolet light. Again, the uncured optical cement is rinsed away. The cured or hardened cement forms the waveguide 40 leading from the optical fiber (to be inserted later) to the dye well. The strip is now ready for the introduction of the dyes. One system for introducing the dye and matrix, that is the gas permeable immobilizing material, into the wells consists simply of masking the entire surface of the strip except for the selected dye well (pH, for example). The dye and matrix is then spread over the surface so that it will get good penetration into each well. The excess is wiped off.

The matrix is cured in situ. This may be done by subjecting it ultraviolet light where the matrix is a substance which can be cured by ultraviolet light. Alernatively, a hardener can be injected by a stepping apparatus of known design.

These sequences of operation are repeated until all three dye well are filled and the matrices are cured.

Alternatively, the dye wells can be filled with the dye and in immobilizer and thereafter covered with a membrane selectively penetrable by the gas to be measured.

Having completed the insertion of the dye, the strip is then sawed into individual probes. Automatic handling equipment can be provided to deliver probes one at a time to an operator station where the operator places an optical fiber 16 in the available channel and secures with optical cement. The optical cement is thereafter cured by ultraviolet light to complete the formation of the probe.

An example of set of dyes and immobilizing matrix is as follows:

| Dye Well | Blood Gas | Dye | Immobilizer Matrix | Excitation Waves |
|---|---|---|---|---|
| 28 | $O_2$ | fluoranthene or coramene | silicone rubber | $\lambda 5$ |
| 29 | $CO_2$(HOPSA) | 8-hydroxy-1,3,6-pyrene tri sulfonic acid | silicone rubber | $\lambda 3$ $\lambda 4$ |
| 30 | pH(HOPSA) | 8-hydroxy-1,3,6-pyrene tri sulfonic acid | Acrylamide gel | $\lambda 1$ $\lambda 2$ |

In the foregoing description of the blood gas probe, there has been disclosed a single fiber probe that interrogates three dye wells each using a fluorescing dye. It should be understood that the invention is equally applicable to systems employing multiple fibers for communicating with respective dye wells such as electrolytes, that the invention is applicable to systems for measuring other blood constituents, and the invention is applicable to systems wherein absorption based dyes are employed to measure the analytes of interest.

BLOOD PRESSURE MONITOR

Figure 6:
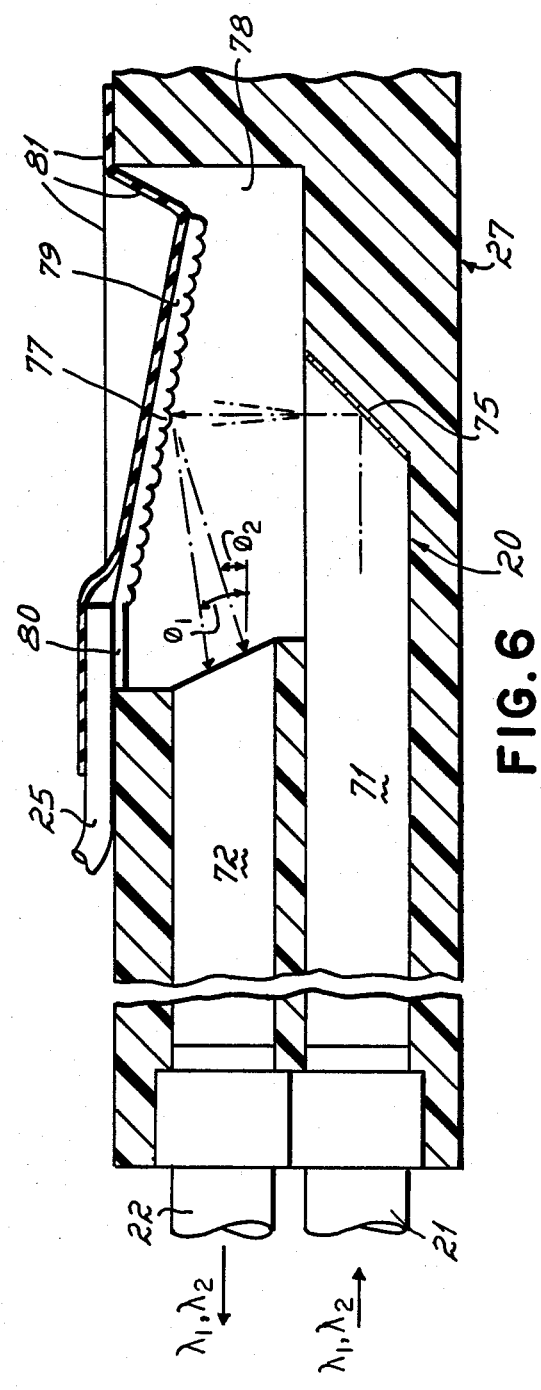
FIG. 6 is a diagrammatic cross sectional veiw of a blood pressure monitoring probe.

The blood pressure monitor is shown in FIG. 6.

The blood pressure probe includes the block 27. Preferably, the block is mounted on the blood gas probe, but it can be a separate unit. The block 27 contains waveguides 71 for two incoming beams and waveguide 72 for two outgoing beams. Each waveguide is connected to a respective optical fiber 21, 22. Wave guide 71 is terminated in a 45° mirror surface 75. An optical diffraction grating 77 is mounted above the mirror surface 75 in a cavity 78. The grating is mounted on a beam 79 which is cantilevered from a position 80 on the block 70. A flexible seal 81 overlies the grating and seals the cavity 78. A source of reference pressure, from tube 25, is connected to the cavity 78 to maintain the cavity at the desired reference pressure such as atmospheric pressure.

The pressure of the blood acts against the flexible seal 81 and causes the grating to flex inwardly. The angular displacement of the grating, flexing inwardly, is a measure of the blood pressure applied to the flexible seal.

Figure 7:
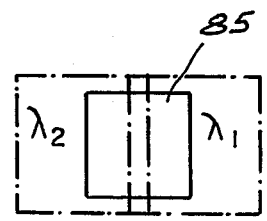
FIG. 7 is a diagrammatic view of the face of a waveguide onto which the light from the diffraction grating is reflected.

In the operation of the blood pressure probe, two beams of wavelengths $\lambda 1$ and $\lambda 2$ are directed through two waveguide 71. Those two beams impinge upon the grating 77. Because of their different wavelengths, the beams will exit from the diffraction grating at differing angles $\phi 1$ and $\phi 2$ for $\lambda 1$ and $\lambda 2$, respectively. As shown in FIG. 7, 85 represents the face of the waveguide 72 upon which the beams impinge and are reflected off the grating. Depending upon the amount of angular shift imparted to the respective beams by the grating, which is in turn dependent upon their wavelengths, the beams will cover greater or lesser portions of the face of the waveguide 72. Thus, varied respective intensities of the beams are transmitted to the insrument 17 (FIG. 1) which provides a measure of the intensity of the beam of wavelength $\lambda 1$ and compares it to the intensity of the beam of wavelength $\lambda 2$. The ratio of the intensity of $\lambda 1$ as compared to $\lambda 2$ will be a measure of the amount of deflection of the grating 77 and, hence, blood pressure.

Each probe would be calibrated with a calibration number, or an identifying electronic tag, attached to it and as it was applied to the monitor. A gain adjustment in the monitor would have to be made to accommodate variations in the calibration of the probes one to the other.

From the above disclosure of the general principles of the present invention and the preceding detailed description of a preferred embodiment, those skilled in the art will readily comprehend the various modifications to which the present invention is susceptible. Therefore, we desire to be limited only by the scope of the following claims and equivalents thereof:

Having described our invention, we claim:

1. A probe for in vivo monitoring constituents of the blood comprising,
    a base having a surface,
    at least one dye well and one channel formed in said base and opening at the surface of said base, said channel also opening into said dye well;
    a first optical fiber having a first end mounted in said channel and a second end opposite said first end,
    a waveguide of optically conducting formed in said medium channel and forming an optical coupling between said fiber and said dye well,
    a dye in said dye well whose optical characteristics change in the presence of a constituent,
    means, permeable to said constituent, for containing said dye within said dye well.

2. Apparatus as in claim 1 further comprising a cannula enclosing a substantial portion of said base and a blood pressure monitoring device mounted on the portion of said base located within said cannula and additional optical fibers connected to said blood pressure monitoring device.

3. Apparatus as in claim 2 further comprising means for continuously supplying a heparin or like solution through said cannula.

4. A probe as in claim 1 in which a plurality of dye wells are formed in said base, each said dye well having a different dye and permeable means combination from the other dye wells for monitoring a plurality of different constituents.

5. A probe as in claim 4 in which each said dye fluoresces when excited by a light beam, said base having an $O_2$ monitoring dye well containing an $O_2$ sensitive dye which is insensitive to $CO_2$ and immobilized in a silicone rubber matrix,
    said base having a $CO_2$ monitoring dye well having a $CO_2$ sensitive dye which is insensitive to $O_2$ in a silicone rubber matrix,
    and said base having a pH monitoring dye well having a hydrophilic dye sensitive only to pH and immobilized in a hydrophilic matrix.

6. Apparatus as in claim 5 further comprising,
    a source of light adjacent said second end of said first optical fiber and directed into said optical fiber, said source having two wavelengths which when directed sequentially onto a dye capable of fluorescing will each produce a fluorescence of differing wavelength, the intensity of fluorsecence for one wavelength of light being different from the intensity of fluorescence for the other wavelength of light,
    wherein the ratio of said different intensities will vary with concentration of a constituent in the dye but remain constant for each specific concentration of said constituent regardless of variations in the intensity of the excitation light.
    and means adjacent said second end of said first optical fiber for measuring the ratio of intensities of said fluorescence of different wavelengths, whereby the concentration of said constituent can be determined.

7. A probe as in claim 1 in which said base is about 50 mm long, 0.5 mm wide and 0.4 mm thick.

8. A probe as in claim 4 wherein said at least one dye well comprises three dye wells and wherein said channel includes a first portion optically coupled to said first end of said optical fiber and a second portion having three channel branches optically coupled to said first portion and respective ones of said three dye wells.

9. A probe as in claim 8 in which said waveguides are square in cross section and said optical fiber is circular in cross section, wherein said fiber has a core having a diameter equal to the length of a side of said square.

10. A probe for monitoring three fluids comprising,
a base having a surface,
three dye wells formed in said base and opening at the surface of said base,
channels formed in said base opening at the surface of said base and to each of said dye wells, said channels containing an optically conducting medium;
optical fiber means for directing light into and receiving light from said dye wells via said optically conducting medium;
a dye in each said dye well,
each dye in each well being capable of reacting to a respective fluid to be monitored to modify the optical characteristics of the dye,
and a membrane covering each dye well,
each membrane being selectively permeable to a fluid being monitored.

11. A probe according to claim 10,
means for directing light into said optical fiber means and waveguides to interrogate the dye in said dye well,
an optoelectronic means for receiving light from said dye wells via said waveguides and optical fiber means, and for analyzing said receiving light for continuously monitoring the respective fluids in the environment surrounding said base.

* * * * *

UNITED STATES PATENT AND TRADEMARK OFFICE
CERTIFICATE OF CORRECTION

PATENT NO. : 4,854,321
DATED : August 8, 1989
INVENTOR(S) : Anthony A. Boiarski

It is certified that error appears in the above-identified patent and that said Letters Patent is hereby corrected as shown below:

```
Column 1, line 7, "relate" should be -- relates --

Column 2, line 8, "dye walls" should be -- dye wells --

Column 2, line 17, "dye walls" should be -- dye wells --

Column 2, line 18, "dye walls" should be -- dye wells --

Column 2, line 53, "blodd" should be -- blood --

Column 5, line 68, "will ber" should be -- will be --

Column 6, line 4, "on of" should be -- One of --

Column 6, line 10, "60is" should be -- 60 is --

Column 6, line 49, "subjecting it" should be --subjecting
it to --

Column 8, line 17, insert "medium" after conducting
Column 8, claim 1, line 18, delete "medium" and delete "and".
```

Signed and Sealed this

Twenty-sixth Day of June, 1990

*Attest:*

HARRY F. MANBECK, JR.

*Attesting Officer*   *Commissioner of Patents and Trademarks*